United States Patent [19]

Durant et al.

[11] 4,090,026
[45] May 16, 1978

[54] CERTAIN NITROGEN HETEROCYCLIC ISOTHIOCYANATE ESTERS

[75] Inventors: Graham John Durant; Charon Robin Ganellin, both of Welwyn Garden City; George Raymond White, Harpenden, all of England

[73] Assignee: Smith Kline & French Laboratories Limited, Welwyn Garden City, England

[21] Appl. No.: 714,210

[22] Filed: Aug. 13, 1976

Related U.S. Application Data

[62] Division of Ser. No. 603,881, Aug. 11, 1975, abandoned.

[30] Foreign Application Priority Data

Sep. 2, 1974 United Kingdom ............... 38255/74

[51] Int. Cl.$^2$ .................. C07D 233/24; C07D 213/53

[52] U.S. Cl. ............................. 548/342; 260/294.8 E; 260/294.8 H; 260/306.8 A; 260/306.8 D; 260/306.8 R; 260/307 H; 260/308 R

[58] Field of Search ................. 260/294.8 H, 294.8 E, 260/309, 306.8 R, 306.8 D, 306.8 A, 307 R, 307 H, 308 R; 548/342

[56] References Cited

U.S. PATENT DOCUMENTS

| 2,923,712 | 2/1960 | Mizzoni | 260/294.8 H |
|---|---|---|---|
| 3,028,391 | 4/1962 | Rorig | 260/294.8 H |
| 3,736,331 | 5/1973 | Black et al. | 260/309 |
| 3,932,443 | 1/1976 | White | 260/309 |

*Primary Examiner*—Alan L. Rotman
*Attorney, Agent, or Firm*—Joan S. Keps; Richard D. Foggio; William H. Edgerton

[57] ABSTRACT

Process for preparing thioureas by treating isothiocyanates with ammonia and alkylamines. A specific product is N-methyl-N'-[2-((5-methyl-4-imidazolyl)methylthio)ethyl]thiourea, useful as a histamine $H_2$-antagonist.

2 Claims, No Drawings

CERTAIN NITROGEN HETEROCYCLIC ISOTHIOCYANATE ESTERS

This is a division of application Ser. No. 603,881, filed Aug. 11, 1975, now abandoned.

This invention relates to an improved chemical process. In particular it relates to an improved process for the production of certain pharmacologically active thiourea compounds.

In British patent specification No. 1,338,169 thioureas have been described including, inter alia, compounds of the following formula:

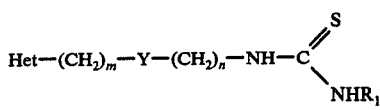

FORMULA I wherein Het is a nitrogen-containing 5 or 6 membered heterocyclic ring such as imidazole, pyridine, thiazole, isothiazole, oxazole, isoxazole, triazole or thiadiazole which ring is optionally substituted by lower alkyl, hydroxyl or halogen; $m$ is 0, 1 or 2 and $n$ is 2 or 3 provided that the sum of $m$ and $n$ is 3 or 4; Y is oxygen or sulphur and $R_1$ is hydrogen or lower alkyl, such as methyl.

Throughout the present specification by the term lower alkyl we refer to an alkyl group containing from 1 to 4 carbon atoms.

A number of processes for the production of compounds of Formula I were also described in British patent specification No. 1,338,169. In particular there was disclosed the process wherein an amine of Formula II:

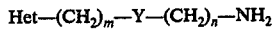

FORMULA II wherein Het, Y, $m$ and $n$ have the same significance as in Formula I is reacted with an isothiocyanate of formula $R_1NCS$ wherein $R_1$ has the same significance as in Formula I. Some disadvantages may be associated with the use of compounds of formula $R_1NCS$ in a chemical process and it is an object of the present invention to provide an alternative process for the production of compounds of Formula I.

Accordingly we provide a process for the production of a thiourea of Formula I in which a compound of the following Formula III:

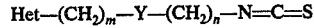

FORMULA III wherein Het, Y, $m$ and $n$ have the same significance as in Formula I is reacted with an amine of formula $R_1NH_2$, wherein $R_1$ has the same significance as in Formula I.

It will be understood that many of the compounds produced and used as starting materials in the process of our invention may exist in the form of an acid addition salt.

The process of the present invention is advantageous using ammonia and lower alkylamines as these are particularly readily available and easy to work with.

Our process may be carried out in the absence of a solvent but may be conveniently carried out in an appropriate solvent such as water, ethanol, isopropanol, or acetonitrile. A solvent is particularly preferred when using ammonia or methylamine.

The process of the present invention is particularly useful in the production of those compounds of Formula I wherein Het is an imidazole, pyridine, thiazole or isothiazole ring, which ring is optionally substituted by lower alkyl, chlorine or bromine. Compounds of Formula I wherein Y is sulphur are preferred products of the process. Compounds wherein $m$ is 1 and $n$ is 2 are also preferred. The process for the production of those compounds of Formula I wherein $R_1$ is hydrogen is particularly advantageous over the process described in British patent specification No. 1,338,169 since the latter process involves a two-step method requiring the use of benzoyl isothiocyanate and subsequent hydrolysis of the product.

Specific compounds which may be made by the present process are the following

N-methyl-N'-[2-((5-methyl-4-imidazolyl)methylthio)ethyl]thiourea
N-methyl-N'-[2-(4-imidazolylmethylthio)ethyl]thiourea
N-methyl-N'-[2-((5-bromo-4-imidazolyl)methylthio)ethyl]thiourea
N-methyl-N'-[2-((1-methyl-2-imidazolyl)methylthio)ethyl]thiourea
N-methyl-N'-[2-(2-imidazolyl)methylthio)ethyl]thiourea
N-methyl-N'-[2-((2-thiazolyl)methylthio)ethyl]thiourea
N-methyl-N'-[2-((3-hydroxy-2-pyridyl)methylthio)ethyl]thiourea
N-methyl-N'-[2-((3-(1,2,4)-triazolyl)methylthio)ethyl]thiourea
N-methyl-N'-[3-(2-thiazolyl)thiopropyl]thiourea
N-methyl-N'-[2-(3-isothiazolylmethylthio)ethyl]thiourea
N-methyl-N'-[2-(3-isoxazolylmethylthio)ethyl]thiourea
N-methyl-N'-[2-((2-(1,3,4)-thiadiazolyl)methylthio)ethyl]thiourea
N-[2-((5-methyl-4-imidazolyl)methylthio)ethyl]thiourea
N-ethyl-N'-[2-((5-methyl-4-imidazolyl)methylthio)ethyl]thiourea.

The isothiocyanates of Formula III may be prepared from a dithiocarbamic acid of Formula IV:

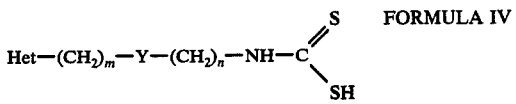

FORMULA IV wherein Het, Y, $m$ and $n$ have the same significance as in Formula I, by treatment with a reagent such as a carbodiimide, e.g. N,N'-dicyclohexylcarbodiimide. The latter reaction is carried out using a suitable solvent, such as acetonitrile, pyridine or dimethylformamide, and the reaction product may be treated without further purification with the amine $R_1NH_2$ wherein $R_1$ has the same significance as in Formula I to yield the compounds of Formula I. The present invention therefore also relates to the overall process for the production of compounds of Formula I from compounds of Formula IV or from the precursor amines of Formula II. Compounds of Formula IV may be prepared, in situ if desired, by reaction of carbon disulphide with the corresponding amine of Formula II.

As stated in British patent specification No. 1,338,169, the compounds of Formula I (which may be produced by the present process) are pharmacologically active for example as histamine H$_2$-antagonists (see Nature 1972, 236, 385), and they are useful for example as inhibitors of gastric acid secretion. For administration they will of course be made up in suitable pharmaceutically acceptable unit dosage forms.

The compounds of Formula I are also useful as intermediates in the production of cyanoguanidine compounds. For example N-methyl-N'-[2-((5-methyl-4-imidazolyl)methylthio)ethyl]thiourea may be reacted with a heavy metal salt of cyanamide such as lead cyanamide to yield N-cyano-N'-methyl-N''-[2-((5-methyl-4-imidazolyl)methylthio)ethyl]guanidine, or N-methyl-N'-[2-((5-methyl-4-imidazolyl)methylthio)ethyl]thiourea may be alkylated and the resultant isothiourea treated with a strong base and cyanamide to give N-cyano-N'-methyl-N''-[2-((5-methyl-4-imidazolyl)methylthio)ethyl]guanidine.

The invention is illustrated but in no way limited by the following examples, wherein all temperatures are given in degrees Centigrade.

EXAMPLE 1

(a)

(i) A solution of 2((5-methyl-4-imidazolyl)methylthio)ethylamine (3.42 g, 0.02 mol) in dry pyridine (15 ml) was slowly added under dry nitrogen to a stirred solution of dicyclohexylcarbodiimide (4.12 g, 0.02 mol) and carbon disulphide (20 ml) in dry pyridine (10 ml) at −10°. After being stirred for 4 hours at −10° then 18 hours at room temperature the cooled (0°) reaction mixture was filtered from dicyclohexylthiourea which was washed with ether. The combined filtrate and washings were evaporated under reduced pressure to dryness, traces of pyridine being removed by azeotropic distillation with water (50 ml) then isopropanol (50 ml). The residue was heated with acetonitrile (25 ml) and cooled to 0°, filtered and the filtrate was heated with excess ethanolic hydrogen chloride, then evaporated again to dryness. Recrystallisation of the residue from acetonitrile gave 5-methyl-4-(2-isothiocyanatoethylthiomethyl)imidazole hydrochloride (2.5 g) m.p. 150°–151°.

(Found: C,38.6; H,5.1; N,17.0; S,25.5; Cl 14.1; C$_8$H$_{11}$N$_3$S$_2$.HCl requires C,38.5; H,4.8 N,16.8; S,25.7; Cl,14.2%).

(ii) A solution of 2-((5-methyl-4-imidazolyl)methylthio)ethylamine (10.2 g) in ethanol (75 ml) was added slowly, with stirring, to carbon disulphide (200 ml). The mixture was set aside overnight at room temperature and the solid formed was collected and recrystallised from aqueous isopropyl alcohol to afford N-[2-((5-methyl-4-imidazolyl)methylthio)ethyl]dithiocarbamic acid (9.8 g), m.p. 127°–129°. This was treated with dicyclohexylcarbodiimide in dry pyridine at −10°, and the mixture was filtered. The filtrate was evaporated to dryness and the residue was treated sith ethanolic hydrogen chloride to give 5-methyl-4-(2-isothiocyanatoethylthiomethyl)imidazole hydrochloride.

(b)

A solution of 5-methyl-4-(2-isothiocyanatoethylthiomethyl)imidazole hydrochloride (50 mg, 0.2 mmol) in 25% aqueous methylamine solution (1.5 ml, excess) was refluxed for 5 minutes then cooled to 0°. N-Methyl-N'-[2-(5-methyl-4-imidazolylmethylthio)ethyl]thiourea (42 mg, 86%), m.p. 146°–8° separated out.

After recrystallisation from water it had m.p. 152°–3°.

EXAMPLE 2

A solution of 2-((5-methyl-4-imidazolyl)methylthio)ethylamine (3.42 g 0.02 mol) in dry pyridine (15 ml) was slowly added under dry nitrogen to a stirred solution of N,N'-dicyclohexylcarbodiimide (4.12 g 0.02 mol) and carbon disulphide (20 ml) in dry pyridine (10 ml) at −10°. The mixture was stirred for 4 hours at −10° and 18 hours at room temperature and was filtered. The filtrate was evaporated to dryness and the residue was dissolved in warm acetonitrile and the solution was cooled, filtered and the filtrate was evaporated to dryness. The residue was boiled for five minutes with an excess of aqueous methylamine. The solid which crystallised on cooling was recrystallised from water to give N-methyl-N'-[2-(5-methyl-4-imidazolylmethylthio)ethyl]thiourea.

EXAMPLE 3

Substitution of a. 2-(4-imidazolylmethylthio)ethylamine
b. 2-(5-bromo-4-imidazolylmethylthio)ethylamine
c. 2-((1-methyl-2-imidazolyl)methylthio)ethylamine
d. 2-(2-imidazolylmethylthio)ethylamine
e. 2-(2-thiazolylmethylthio)ethylamine
f. 2-(3-hydroxy-2-pyridylmethylthio)ethylamine
g. 2-(3-(1,2,4)-triazolylmethylthio)ethylamine
h. 3-(2-thiazolyl)thiopropylamine
i. 2-(3-isothiazolylmethylthio)ethylamine
j. 2-(3-isoxazolylmethylthio)ethylamine
k. 2-(4-imidazolylethylthio)ethylamine for 2-(5-methyl-4-imidazolylmethylthio)ethylamine in the general procedures of Examples 1 and 2 leads to the production of:

a. N-methyl-N'-[2-(4-imidazolylmethylthio)ethyl]thiourea
b. N-methyl-N'-[2-((5-bromo-4-imidazolyl)methylthio)ethyl]thiourea
c. N-methyl-N'-[2-((1-methyl-2-imidazolyl)methylthio)ethyl]thiourea
d. N-methyl-N'-[2-(2-imidazolyl)methylthio)ethyl]thiourea
e. N-methyl-N'-[2-((2-thiazolyl)methylthio)ethyl]thiourea
f. N-methyl-N'-[2-((3-hydroxy-2-pyridyl)methylthio)ethyl]thiourea
g. N-methyl-N'-[2-((3-(1,2,4)-triazolyl)methylthio)ethyl]thiourea
h. N-methyl-N'-[3-(2-thiazolyl)thiopropyl]thiourea
i. N-methyl-N'-[2-(3-isothiazolylmethylthio)ethyl]thiourea
j. N-methyl-N'-[2-(3-isoxazolylmethylthio)ethyl]thiourea
k. N-methyl-N'-[2-(4-imidazolylethylthio)ethyl]thiourea.

EXAMPLE 4

Substitution of ethylamine and butylamine for methylamine in the procedures of Examples 1(b) and 2 leads to the production of N-ethyl-N'-[2-((5-methyl-4-imidazolyl)methylthio)ethyl]thiourea and N-butyl-N'-

[2-((5-methyl-4-imidazolyl)methylthio)ethyl]thiourea, respectively.

EXAMPLE 5

Substitution of ammonia for methylamine in the procedures of Examples 1(b) and 2 leads to the production of N-[2-((5-methyl-4-imidazolyl)methylthio)ethyl]thiourea.

EXAMPLE 6 a. Phosphoryl chloride (87 ml) was added dropwise to a vigorously stirred mixture of thiosemicarbazide (100 g), methoxyacetic acid (100 g) and petroleum ether b.p. 80°–100° (200 ml) maintained at 60°–70°. The temperature of the mixture was slowly raised to 95° and was kept at this temperature until the evolution of gas ceased. The solvent was evaporated and the residual syrup was dissolved in water (200 ml) to give a yellow solution which was adjusted to pH 7 by the addition of 10N NaOH. The mixture was filtered to give 5-amino-2-methoxymethyl-(1,3,4)-thiadiazole (111.25 g). Recrystallisation from water gave compound with m.p. 177°–179°.

(Found: C, 32.9; H, 4.8; N, 29.1; S, 22.0; $C_4H_7N_3OS$ requires: C, 33.1; H, 4.9; N, 29.0; S, 22.1%).

b. An intimate dry mixture of 5-amino-2-methoxymethyl-(1,3,4)-thiadiazole (34.8 g) and sodium nitrite (75.9 g) was added over 1.5 hours to a stirred mixture of hydrobromic acid (48%, 270 ml) and cuprous bromide (2 g) maintained at −7°. The mixture was stirred at −6° for 1 hour and at room temperature for 1.5 hours. The mixture was neutralised with 10M NaOH, treated with sodium metabisulphite, warmed to 60° for 20 min., reneutralised with sodium hydroxide and filtered. The filtrate was extracted with cyclohexane for 13 hours, and the cyclohexane extract was dried over calcium sulphate, filtered and evaporated to give 5-bromo-2-methoxymethyl(1,3,4)thiadiazole (30.35 g) as an oil.

(Found: C, 23.0; H, 2.7; Br 38.0; N, 13.5; S, 15.1; $C_4H_5BrN_2OS$ requires C, 23.0; H, 2.4; Br 38.2; N, 13.4; S, 15.3 %).

c. Zinc dust (32.69 g) was added to a stirred solution of 5-bromo-2-methoxymethyl(1,3,4)thiadiazole (51 g) in acetic acid (200 ml) at room temperature. The mixture was warmed gently and a vigorous reaction took place and the mixture was refluxed for 1.5 hours. The mixture was filtered and the residue was washed with boiling water (200 ml). The combined filtrate and washings were neutralised and continuously extracted with ether for 8 hours. The ethereal extract was dried over magnesium sulphate and evaporated to give 2-methoxymethyl(1,3,4)thiadiazole (17.57 g) m.p. 30.5°–32°.

(Found: C, 36.5; H, 4.5; N, 21.4; S, 24.3; $C_4H_6N_2OS$ requires: C, 36.9; H, 4.6; N, 21.5; S, 24.6 %).

d. Equimolar quantities of 2-methoxymethyl(1,3,4)-thiadiazole and cysteamine hydrochloride were refluxed under nitrogen for 42 hours in a three-fold excess of hydrobromic acid (48%). The mixture was evaporated to dryness and the residue was dissolved in water. The solution was adjusted to pH 11 by the addition of IRA 400(OH⁻) and applied to a column of CG50(H⁺) which was eluted with dilute acetic acid. The eluate was evaporated to give 2-(2-(1,3,4)thiadiazolylmethylthio)ethylamine as an oil.

This oil was characterised as a picrate derivative recrystallised from ethanol with m.p. 110°–112° NMR spectrum of picrate in $^2H_6$ dimethyl sulphoxide at 100 mHz:

—C$\underline{H}_2$C$\underline{H}_2$— m at δ2.9 (4.1 protons)
thiadiazole—C$\underline{H}_2$—S— s at δ4.38 (2.0 protons)
N$\underline{H}_2$ s at δ7.8 (2.2 protons)
5-$\underline{H}$-1,3,4-thiadiazole s at δ9.50 (1.0 protons)

e. Substitution of 2-(2-(1,3,4)-thiadiazolylmethylthio)ethylamine for 2-(5-methyl-4-imidazolylmethylthio)ethylamine in the general procedures of Examples 1 and 2 leads to the production of N-methyl-N'-[2-(1,3,4)-thiadiazolylmethylthio)ethyl]thiourea.

EXAMPLE 7

Substitution of 2-(4-imidazolylmethoxy)ethylamine for 2-(5-methyl-4-imidazolylmethylthio)ethylamine in the general procedures of Examples 1 and 2 leads to the production of N-methyl-N'-[2-(4-imidazolylmethoxy)ethyl]thiourea.

What we claim is:

1. A compound of the formula:

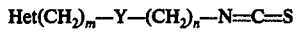

$$Het(CH_2)_m-Y-(CH_2)_n-N=C=S$$

wherein Het is imidazole, pyridine or triazole, which ring is optionally substituted by lower alkyl, hydroxyl or halogen; m is 0, 1 or 2 and n is 2 or 3 provided that the sum of m and n is 3 or 4 and Y is oxygen or sulphur.

2. A compound of claim 1 wherein Het is 5-methyl-4-imidazole, m is 1, n is 2 and Y is sulphur.

* * * * *